(12) United States Patent
Rabasco et al.

(10) Patent No.: US 11,864,882 B2
(45) Date of Patent: Jan. 9, 2024

(54) BREATH SENSING SYSTEM AND METHODS OF USE

(71) Applicant: BoydSense, Inc., South San Francisco, CA (US)

(72) Inventors: Joel Rabasco, San Bruno, CA (US); Paul Klock, San Bruno, CA (US); Ryan Held, San Bruno, CA (US)

(73) Assignee: BoydSense, Inc., South San Francisco, CA (US)

( * ) Notice: Subject to any disclaimer, the term of this patent is extended or adjusted under 35 U.S.C. 154(b) by 50 days.

(21) Appl. No.: 16/588,298

(22) Filed: Sep. 30, 2019

(65) Prior Publication Data

US 2020/0100702 A1     Apr. 2, 2020

Related U.S. Application Data

(60) Provisional application No. 62/739,755, filed on Oct. 1, 2018.

(51) Int. Cl.
*A61B 5/083*     (2006.01)
*A61B 5/00*      (2006.01)
(Continued)

(52) U.S. Cl.
CPC ............ *A61B 5/083* (2013.01); *A61B 5/0004* (2013.01); *A61B 5/097* (2013.01); *A61B 5/7282* (2013.01); *A61B 5/7445* (2013.01); *A61L 2/10* (2013.01); *A61L 2/26* (2013.01); *A61B 2560/0431* (2013.01); *A61L 2202/11* (2013.01)

(58) Field of Classification Search
None
See application file for complete search history.

(56) References Cited

U.S. PATENT DOCUMENTS

| | | | |
|---|---|---|---|
| 5,224,487 A | * | 7/1993 | Bellofatto ............ A61B 5/0871 128/200.24 |
| 5,922,610 A | | 7/1999 | Alving et al. |

(Continued)

FOREIGN PATENT DOCUMENTS

| | | |
|---|---|---|
| EP | 1558316 B1 | 1/2008 |
| EP | 2281193 A1 | 2/2011 |

(Continued)

*Primary Examiner* — Christian Jang
(74) *Attorney, Agent, or Firm* — Shay Glenn LLP

(57) ABSTRACT

The systems and methods described herein can advantageously allow users to discretely measure their exhaled breath in an easy, cost-effective and non-invasive manner. A handheld breath sensing system may be provided with a main housing, a first mouthpiece, a lid, a sampling chamber, a sensor and a microprocessor. The first mouthpiece may be configured to allow a user to exhale into the mouthpiece. The lid may be movable between an open position and a closed position. The sampling chamber may be in fluid communication with the first mouthpiece. The sensor may be in fluid communication with the sampling chamber and configured to measure at least one property of a user's breath. The microprocessor may be configured to process electronic signals from the sensor such that at least one volatile organic compound in the user's breath can be quantified and a resulting biomarker measurement provided to the user in near real-time.

20 Claims, 10 Drawing Sheets

(51) Int. Cl.
*A61L 2/26* (2006.01)
*A61L 2/10* (2006.01)
*A61B 5/097* (2006.01)

(56) References Cited

U.S. PATENT DOCUMENTS

| | | | |
|---|---|---|---|
| 8,366,630 B2 | 2/2013 | Haick et al. | |
| 8,481,324 B2 | 7/2013 | Haick et al. | |
| 8,796,034 B2 | 8/2014 | von Bahr et al. | |
| 8,945,935 B2 | 2/2015 | Haick et al. | |
| 8,999,244 B2 | 4/2015 | Haick et al. | |
| 9,315,848 B2 | 4/2016 | Haick et al. | |
| 9,365,419 B2 | 6/2016 | Haick et al. | |
| 9,528,979 B2 | 12/2016 | Haick et al. | |
| 9,551,712 B2 | 1/2017 | Haick et al. | |
| 9,678,059 B2 | 6/2017 | Haick et al. | |
| 9,689,826 B2 | 6/2017 | Haick et al. | |
| 9,696,311 B2 | 7/2017 | Haick et al. | |
| D876,258 S | 2/2020 | Rabasco et al. | |
| 2003/0208133 A1* | 11/2003 | Mault | A61B 5/097 600/532 |
| 2004/0025899 A1 | 2/2004 | Pinsky | |
| 2007/0142739 A1 | 6/2007 | Sonnenberg et al. | |
| 2009/0137919 A1 | 5/2009 | Bar-Lavie et al. | |
| 2009/0311149 A1 | 12/2009 | Freedgood | |
| 2010/0012417 A1 | 1/2010 | Walter et al. | |
| 2010/0191474 A1 | 7/2010 | Haick | |
| 2010/0198521 A1 | 8/2010 | Haick | |
| 2011/0302992 A1* | 12/2011 | Robbins | G01N 21/3504 73/23.3 |
| 2012/0021375 A1* | 1/2012 | Binner | A61C 17/065 433/89 |
| 2013/0171733 A1 | 7/2013 | Haick et al. | |
| 2014/0216136 A1 | 8/2014 | Yim | |
| 2015/0097701 A1* | 4/2015 | Al-Ali | G06F 21/84 340/870.07 |
| 2015/0301021 A1 | 10/2015 | Haick et al. | |
| 2016/0100774 A1* | 4/2016 | Wilcox | G16H 50/30 600/532 |
| 2016/0106343 A1 | 4/2016 | Wondka et al. | |
| 2016/0146779 A1 | 5/2016 | Gallagher et al. | |
| 2016/0150995 A1 | 6/2016 | Ratto et al. | |
| 2016/0367767 A1 | 12/2016 | Cashman et al. | |
| 2017/0135605 A1* | 5/2017 | Sandholt | A61B 5/7435 |
| 2017/0160265 A1 | 6/2017 | Haick et al. | |
| 2017/0164878 A1 | 6/2017 | Connor | |
| 2017/0164892 A1 | 6/2017 | Sezan et al. | |
| 2017/0188875 A1 | 7/2017 | Banet et al. | |
| 2017/0192008 A1 | 7/2017 | Silkaitis et al. | |
| 2017/0238815 A1* | 8/2017 | Luxon | A61B 5/024 |
| 2018/0140786 A1 | 5/2018 | Calderon Oliveras et al. | |
| 2018/0164283 A1 | 6/2018 | Godula-Jopek et al. | |

FOREIGN PATENT DOCUMENTS

| | | |
|---|---|---|
| EP | 1978871 B1 | 5/2015 |
| JP | 2016126055 A | 7/2016 |
| WO | WO2009/013754 A1 | 1/2009 |
| WO | WO2010/104305 A2 | 9/2010 |

* cited by examiner

BREATH SENSING SYSTEM AND METHODS OF USE

CROSS REFERENCE TO RELATED APPLICATIONS

This application claims priority to U.S. Provisional Patent Application No. 62/739,755, filed Oct. 1, 2018, titled "BREATH SENSING SYSTEM AND METHODS OF USE", which is hereby incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are systems for measuring elements of human breath, and more particularly small, handheld consumer devices and methods that can be used to measure key body biomarkers via exhaled breath.

BACKGROUND

Metabolic syndrome is a global health crisis costing trillions of dollars, and a common precursor to cardiovascular disease and diabetes. By the time just one patient develops diabetes, for example, their average annual cost of treatment jumps from $510 to $10,970. For many metabolic syndrome patients, chronic disease can be prevented through a diet personalized to their unique metabolic response.

While over-the-counter blood glucose and ketone meters are widely available, and can be used to track metabolic response to food, they aren't often used for this purpose. One reason for this is that the devices and test strips are expensive, and require a painful finger prick to produce a blood sample. If economical, non-invasive technology were to become available, more consumers would take advantage of the opportunity to track and measure their metabolic response to food, using the information to fine-tune their diet and achieve their health goals. By understanding how diet and exercise affects their metabolism, people with chronic disease could better maintain their health.

Accordingly, what is needed and is not provided by the prior art are systems for easily measuring a user's metabolic response to food and other activities in a cost-effective and non-invasive manner.

SUMMARY OF THE DISCLOSURE

Using breath sampling, the systems disclosed herein allow people to measure their specific metabolic response—i.e. blood glucose concentration and level of ketosis—to food and exercise. These systems and methods provide non-invasive and affordable consumer tools to measure key body biomarkers via exhaled breath.

A developing area of biotechnology, breath-based metabolomics focuses on the capture, identification, and quantification of volatile organic compound (VOC) patterns in human breath, and using it to diagnose and monitor chronic diseases. VOCs are a large group of carbon-based molecules in a gas phase at room temperature. VOCs in breath carry a wealth of information about the body's biology and health. Detailed examples of prior art breath sensing devices are provided by U.S. Pat. No. 5,922,610 issued Jul. 13, 1999 and entitled System To Be Used For The Determination Of NO Levels In Exhaled Air And Diagnostic Methods For Disorders Related To Abnormal NO Levels, and U.S. Pat. No. 8,796,034 issued Aug. 5, 2014 and entitled Apparatus and Method for Diagnostic Gas Analysis.

According to aspects of the present disclosure, a truly non-invasive, pain-free, inexpensive handheld device is provided that consumers can use to monitor their body's metabolic reaction to food and exercise. This small, device can extract information from VOCs in exhaled breath that correlate to key body biomarkers—i.e. blood glucose concentration and level of ketosis—and send it to a mobile application, which can analyze and display the data to the consumer in near real-time. The platform uses predictive algorithms and sensors to extract the identified VOCs from the inherent noise found in breath data. This breath-sensing technology and analytics can be applied to many healthcare and wellness applications, including chronic care management and disease detection, and can be configured to measure other parameters in a person's breath.

The systems and methods described herein can advantageously allow users to discretely measure their exhaled breath in an easy, cost-effective and non-invasive manner. According to aspects of the present disclosure, in some embodiments a handheld breath sensing system is provided with a main housing, a first mouthpiece, a lid, a sampling chamber, a sensor and a microprocessor. The first mouthpiece may be located on the main housing and configured to allow a user to exhale into the mouthpiece. The lid may be pivotably mounted to the main housing and movable between an open position in which the first mouthpiece is exposed for use and a closed position in which the first mouthpiece is covered. The sampling chamber may be located within the main housing and in fluid communication with the first mouthpiece. The sensor may be in fluid communication with the sampling chamber and configured to measure at least one property of a user's breath in the sampling chamber. The microprocessor may be electronically coupled to the sensor and configured to process electronic signals from the sensor such that at least one volatile organic compound in the user's breath can be quantified and a resulting biomarker measurement provided to the user in near real-time.

In some embodiments of the above systems, the biomarker measurement is a glucose level. In some embodiments, the biomarker measurement is a ketone level. They system may further include a wireless communication device electronically coupled to the microprocessor thereby allowing the microprocessor to wirelessly communicate with another mobile device. In some embodiments, the other mobile device is a smart phone running a proprietary application associated with the handheld breath sensing system, the application being configured to display the biomarker measurement to the user in near real-time. The system may further include a display located on the main housing or lid, the display being electronically coupled to the microprocessor and configured to display the biomarker measurement to the user in near real-time. In some embodiments, the system further includes a second mouthpiece configured to be interchangeable with the first mouthpiece and an inside portion of the lid is configured to alternately hold the first mouthpiece or the second mouthpiece when not in use.

In some embodiments, the system further includes an ultraviolet germicidal irradiation unit configured to emit a short-wavelength ultraviolet light to kill or inactivate microorganisms located on one or more surfaces of the first mouthpiece. The system may further include a light guide located between the ultraviolet germicidal irradiation unit and the first mouthpiece, the light guide being configured to guide light from the irradiation unit to the first mouthpiece. In some embodiments, the ultraviolet germicidal irradiation unit is configured to emit a short-wavelength ultraviolet light to kill or inactivate microorganisms located on one or more surfaces of a second mouthpiece located in the lid simultaneously with the first mouthpiece.

In some embodiments, the system further comprises an ultraviolet germicidal irradiation unit configured to emit a short-wavelength ultraviolet light to kill or inactivate microorganisms located on one or more surfaces of the sampling chamber. The ultraviolet germicidal irradiation unit may be configured to emit a short-wavelength ultraviolet light to kill or inactivate microorganisms located on one or more surfaces of the first mouthpiece simultaneously with the sampling chamber. In some embodiments, the ultraviolet germicidal irradiation unit is configured to emit a short-wavelength ultraviolet light to kill or inactivate microorganisms located on one or more surfaces of a second mouthpiece located in the lid simultaneously with the sampling chamber and the first mouthpiece.

In some embodiments, the system further includes a multi-pivot hinge configured to pivotably connect the lid to the main housing such that there are no hinge parts protruding from the lid and the main housing when the lid is in the closed position. The main housing and the lid may cooperate to provide a closed volume of less than 8.0 cubic inches.

According to aspects of the present disclosure, in some embodiments a method of sensing a biomarker exhaled from a user includes the step of providing a handheld breath sensing system as recited above. The method further includes pivoting the lid into the open position, exhaling into the first mouthpiece, and using the sensor to measure at least one property of the user's breath in the sampling chamber. The method further includes using the microprocessor to process the electronic signals from the sensor such that the at least one volatile organic compound in the user's breath is quantified, and providing the resulting biomarker measurement to the user in near real-time.

In some embodiments, the method further includes establishing wireless communications between the microprocessor and a smart phone running a proprietary application associated with the handheld breath sensing system, and using the application to display the biomarker measurement to the user in near real-time. The method may further include using a display mounted on the main housing or the lid to display the biomarker measurement to the user in near real-time.

In some embodiments, the method further includes activating an ultraviolet germicidal irradiation unit to emit a short-wavelength ultraviolet light to kill or inactivate microorganisms located on one or more surfaces of the first mouthpiece. The method may further include activating the ultraviolet germicidal irradiation unit to emit a short-wavelength ultraviolet light to kill or inactivate microorganisms located on one or more surfaces of a second mouthpiece located in the lid simultaneously with one or more surfaces on the sampling chamber and the first mouthpiece.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Described herein are small, handheld consumer devices and methods that can be used to measure key body biomarkers via exhaled breath.

Figure 1:
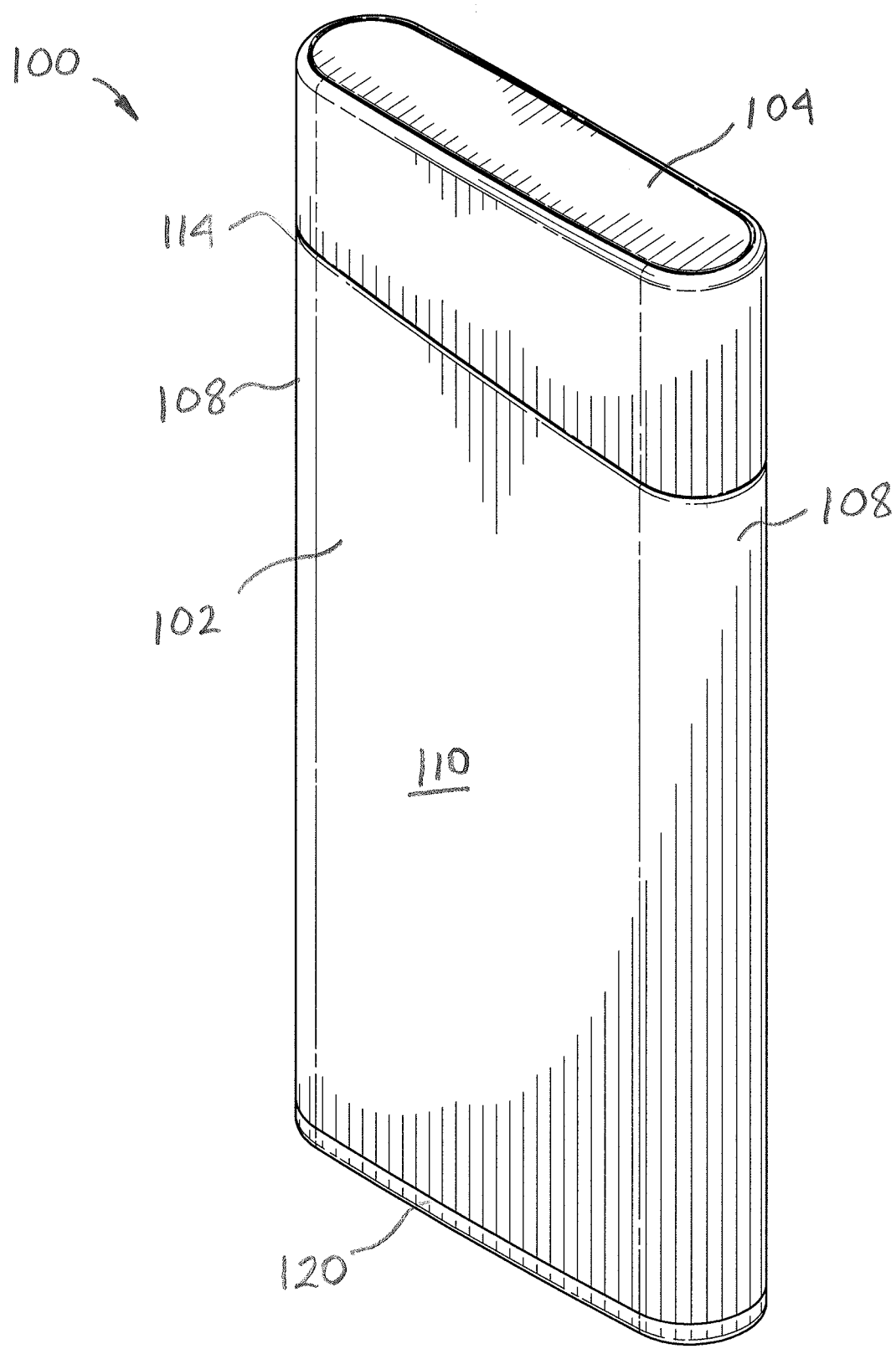
FIG. 1 is an isometric view of an exemplary breath sensing device in accordance with aspects of the present disclosure, showing the device with its pivoting lid in a closed position.
Figure 2:
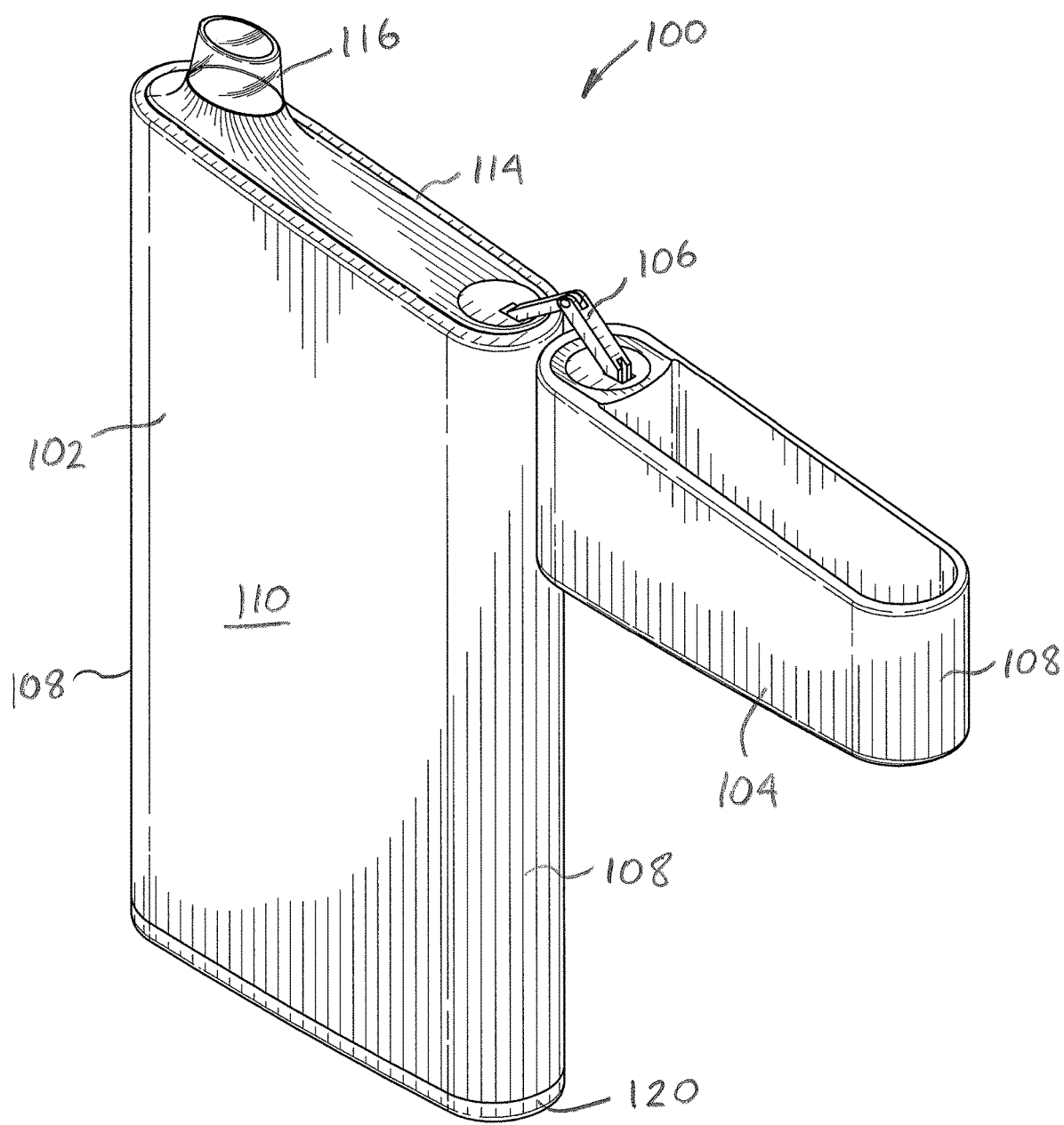
FIG. 2 is an isometric view of the breath sensing device of FIG. 1, showing the device with its pivoting lid in an open position.
Figure 3:
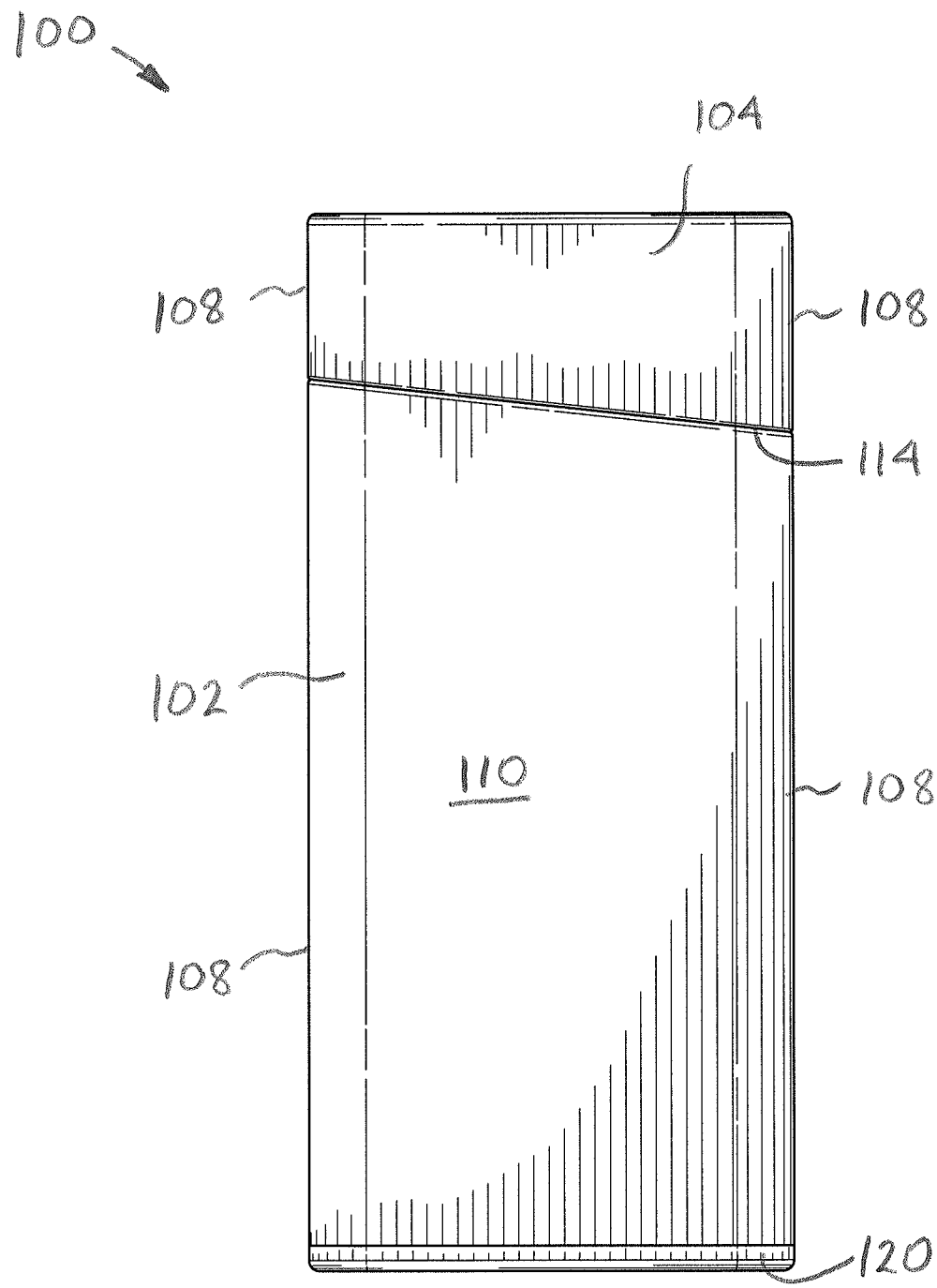
FIG. 3 is a front view of the breath sensing device of FIG. 1, showing the device with its pivoting lid in a closed position. The back view (not shown) is a mirror image of the front view.
Figure 4:
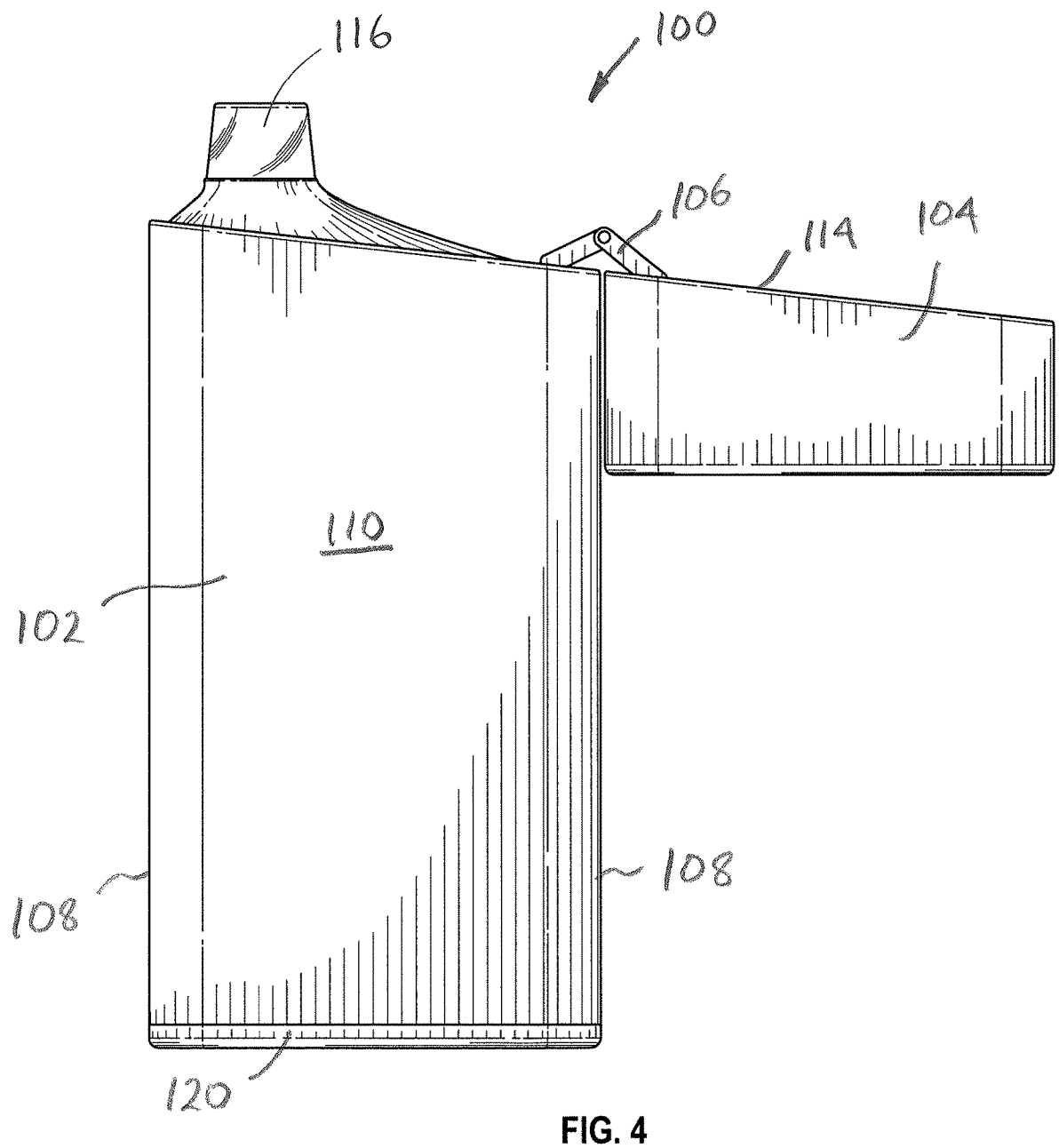
FIG. 4 is a front view of the breath sensing device of FIG. 1, showing the device with its pivoting lid in an open position.
Figures 5, 6:
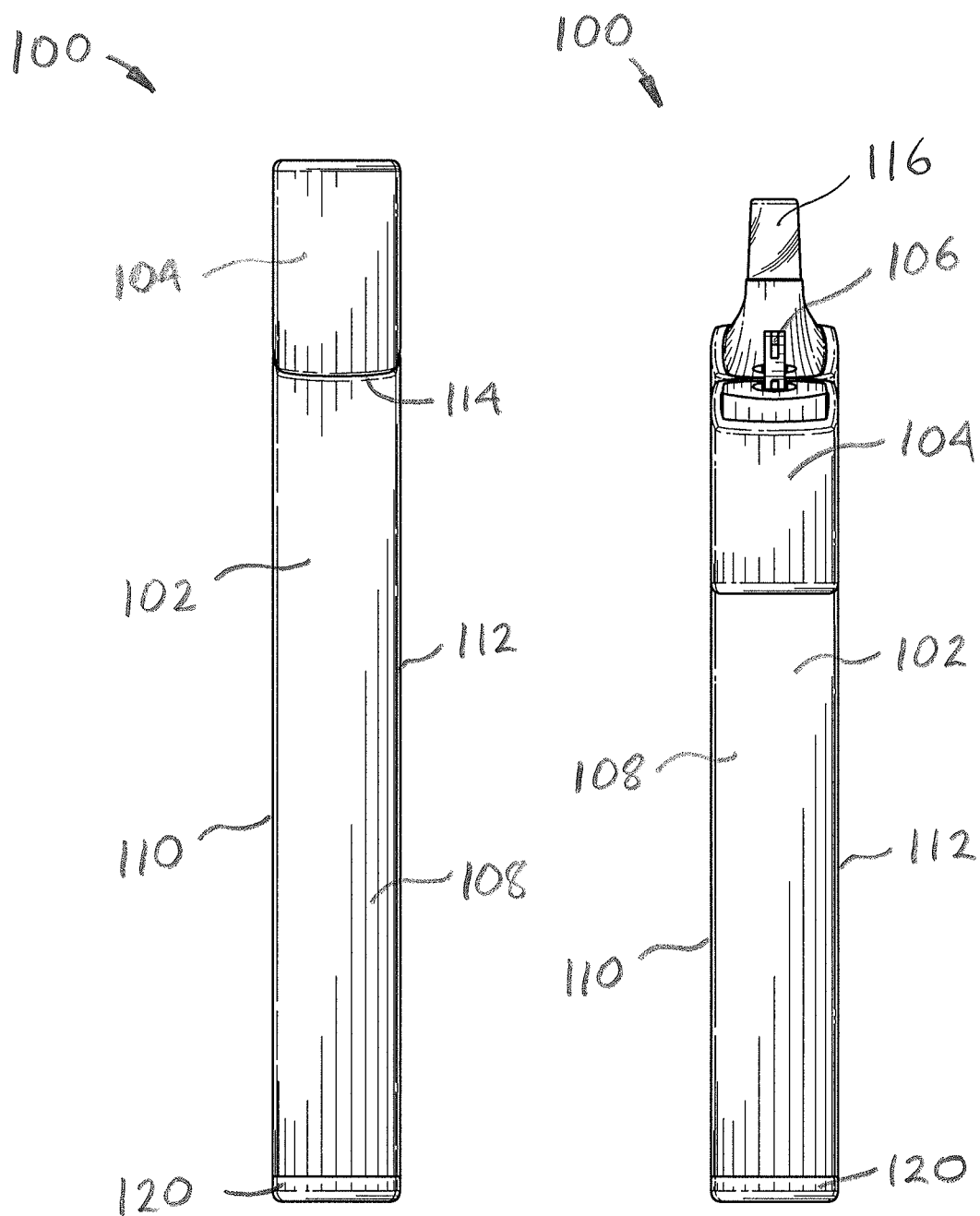
FIG. 5 is a right side view of the breath sensing device of FIG. 1, showing the device with its pivoting lid in a closed position. The left side view (not shown) is similar to the right side view.
FIG. 6 is a right side view of the breath sensing device of FIG. 1, showing the device with its pivoting lid in an open position.
Figure 7:
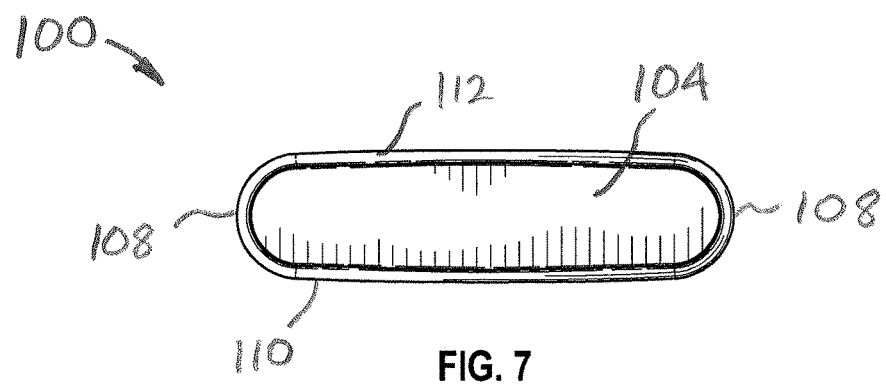
FIG. 7 is a top view of the breath sensing device of FIG. 1, showing the device with its pivoting lid in a closed position.
Figure 8:
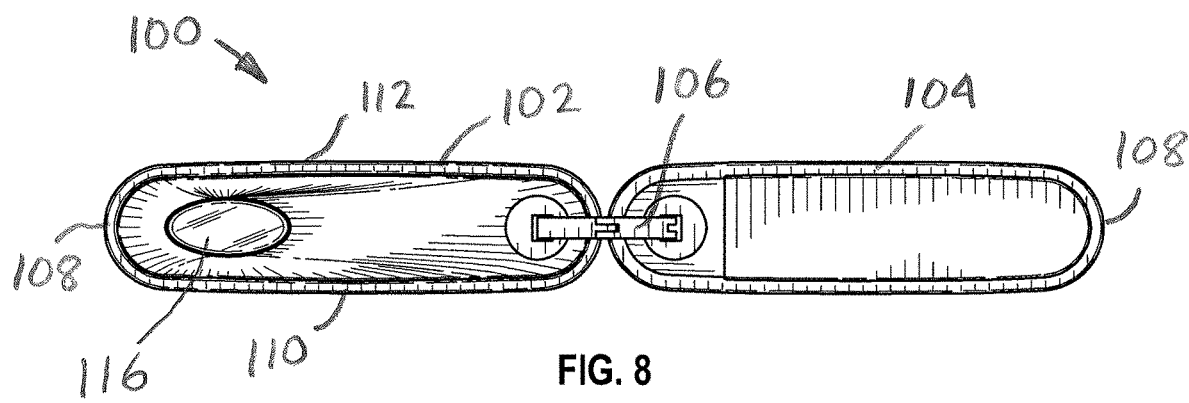
FIG. 8 is a top view of the breath sensing device of FIG. 1, showing the device with its pivoting lid in an open position.
Figure 9:
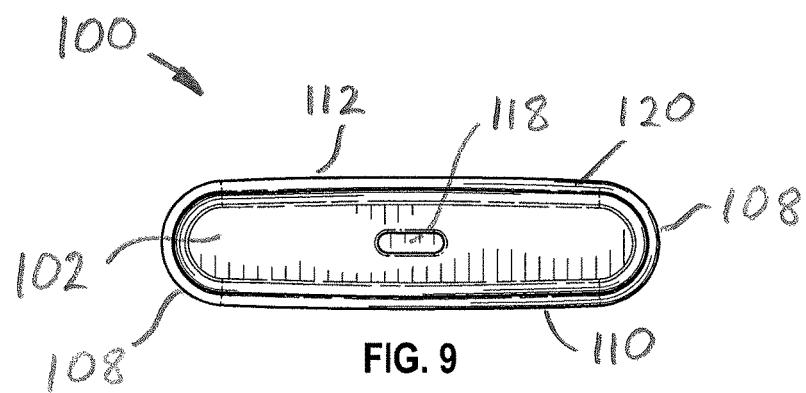
FIG. 9 is a bottom view of the breath sensing device of FIG. 1, showing the device with its pivoting lid in a closed position.

Referring to FIGS. 1-9, an exemplary breath sensing device 100 includes a main housing 102 and a pivoting lid 104. FIGS. 1, 3, 5, 7 and 9 show device 100 with lid 104 in a closed position and FIGS. 2, 4, 6 and 8 show device 100 with lid 104 in an open position. As best seen in FIG. 2, a multi-pivot hinge 106 may be used to connect lid 104 to main housing 102 so that there are no protruding hinge parts to disrupt the clean lines of device 100 when it is in the closed position. In this exemplary embodiment, main housing 102 and lid 104 together form a generally rectangular device having hemi-cylindrical side surfaces 108. As shown in FIG. 7-9, the front surface 110 and back surface 112 each bow slightly outwardly. As best seen in FIG. 2, main housing 102 and lid 104 meet at parting line 114 that forms an 84 degree angle with the side surfaces 108 of main housing 102. Slight bevels may also be provided on both sides of parting line 114 and along the top and bottom edges of device 100, as shown. In this exemplary embodiment, device 100 is 5.25 inches high, 2.40 inches wide, and 0.64 inches thick, resulting in a volume of about 7.6 cubic inches.

As shown in FIGS. 2, 4, 6 and 8, a top surface of main housing 102 may be provided with an upwardly extending mouthpiece 116. During use, a user places mouthpiece 116 between their lips and exhales into the mouthpiece. The user's exhaled breath travels through mouthpiece 116, through channels and sensors (not shown) within main housing 102, and exits through a combination exhaust vent and charging port 118 located on the bottom surface of main housing 102, shown in FIG. 9. As best seen in FIG. 2, at least a portion of mouthpiece 116 may be formed from a transparent plastic for easy sanitizing, as will be subsequently described.

In this exemplary embodiment, an LED band 120 is provided around the entire bottom edge of main housing 102. Band 120 may be illuminated with different colors and/or different timing patterns to provide feedback to the user, as will be subsequently described. Band 120 may be seen by the user when they are exhaling into mouthpiece 116, regardless of the orientation in which device 100 is held. In other embodiments (not shown), LED illumination may be located elsewhere on device 100 and may or may not extend entirely around the device.

Figure 10:
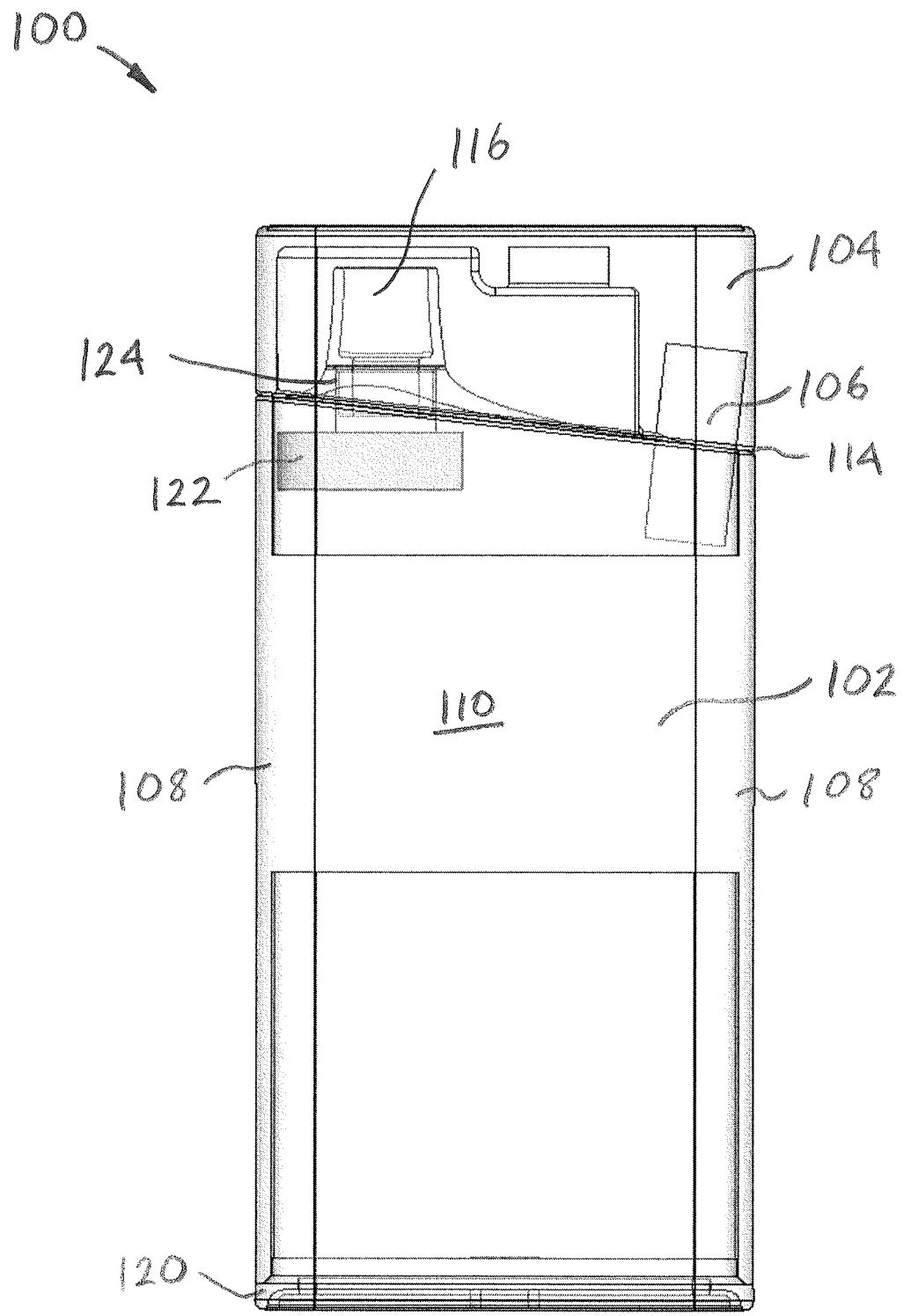
FIG. 10 is a transparent front view of the breath sensing device of FIG. 1, showing some of the interior components of the device.

Referring to FIG. 10, device 100 may be provided with an ultraviolet germicidal irradiation (UVGI) unit 122. UVGI unit 122 may be configured to emit a short-wavelength ultraviolet (UV-C) light to kill or inactivate microorganisms by destroying nucleic acids and disrupting their DNA, leaving them unable to perform vital cellular functions. In this exemplary embodiment, UVGI unit 122 is located inside main housing 102 below mouthpiece 116, and is connected to the bottom of mouthpiece 116 with a clear plastic light guide 124. When UVGI unit 122 is activated during a disinfection cycle, it emits UV-C light upwardly through light guide 124 and mouthpiece 116. In some embodiments, the disinfection cycle cannot be started or continued unless lid 104 is closed. The inside surface 126 of lid 104 (shown in FIGS. 12 and 13) may comprise a polished and/or reflective material or coating so that the UV-C light reflects around the inside of lid 104 and disinfects everything inside it, including all interior and exterior surfaces of mouthpiece 116.

Figure 11:
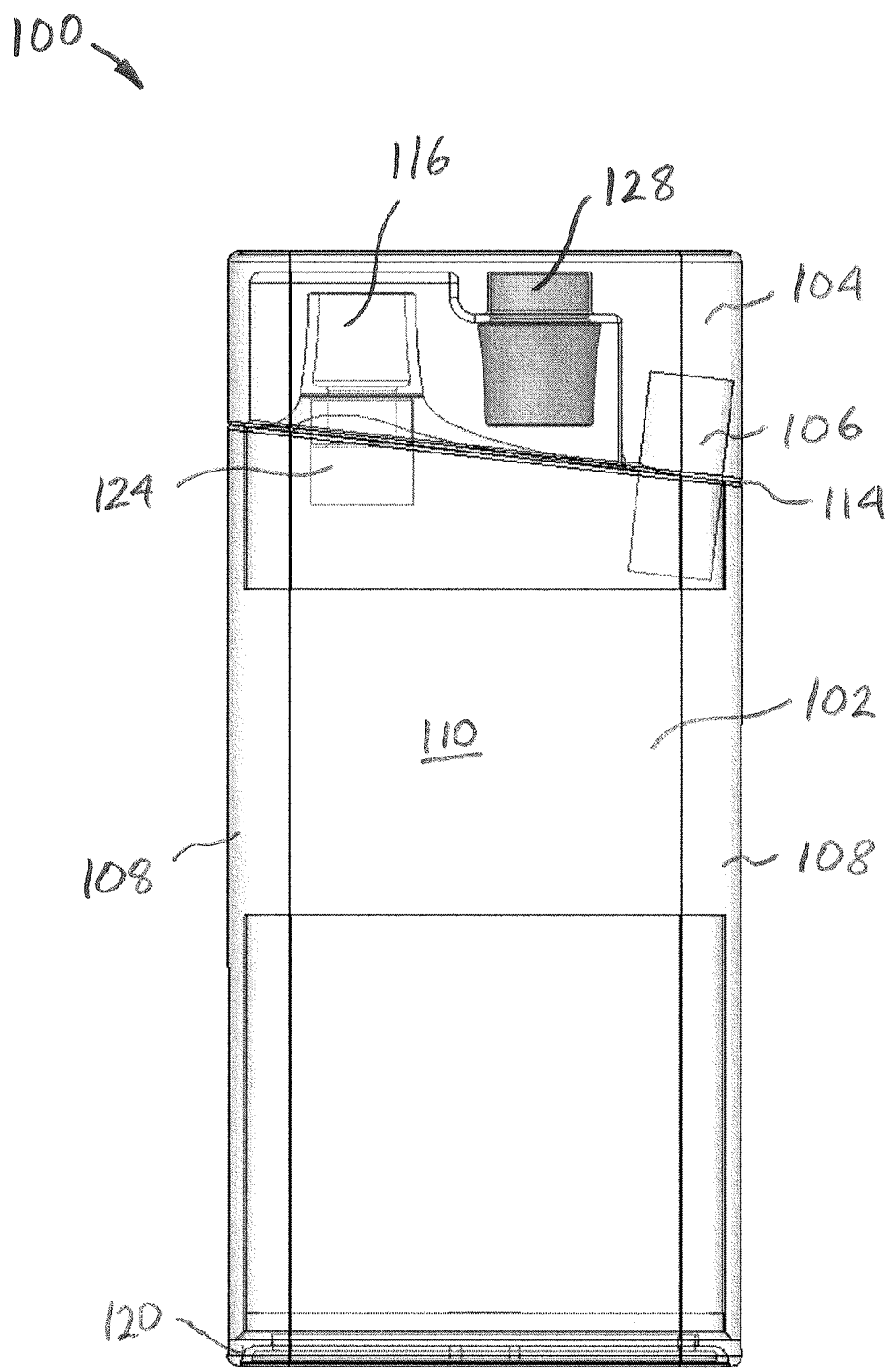
FIG. 11 is a transparent front view of the breath sensing device of FIG. 1, showing different interior components of the device from FIG. 10.
Figure 12:
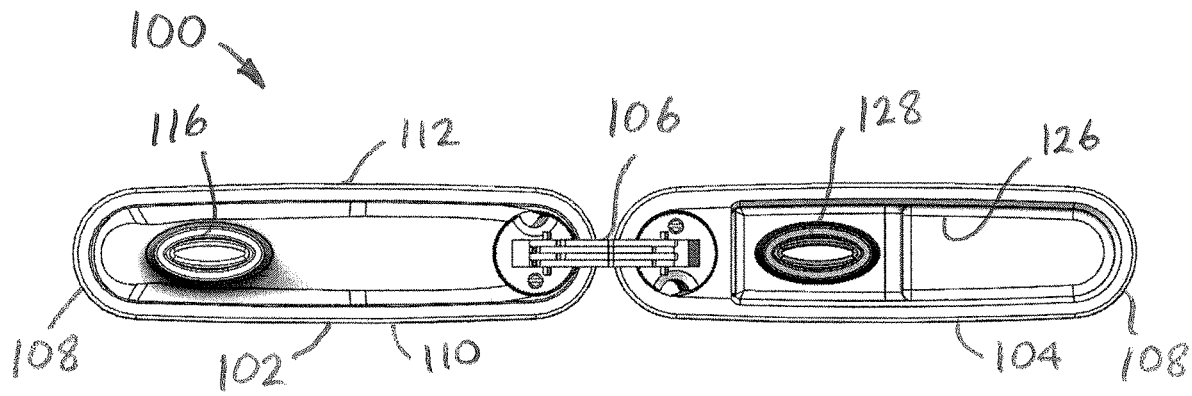
FIG. 12 is a top view of the breath sensing device of FIG. 1, showing the device with its pivoting lid in an open position.
Figure 13:
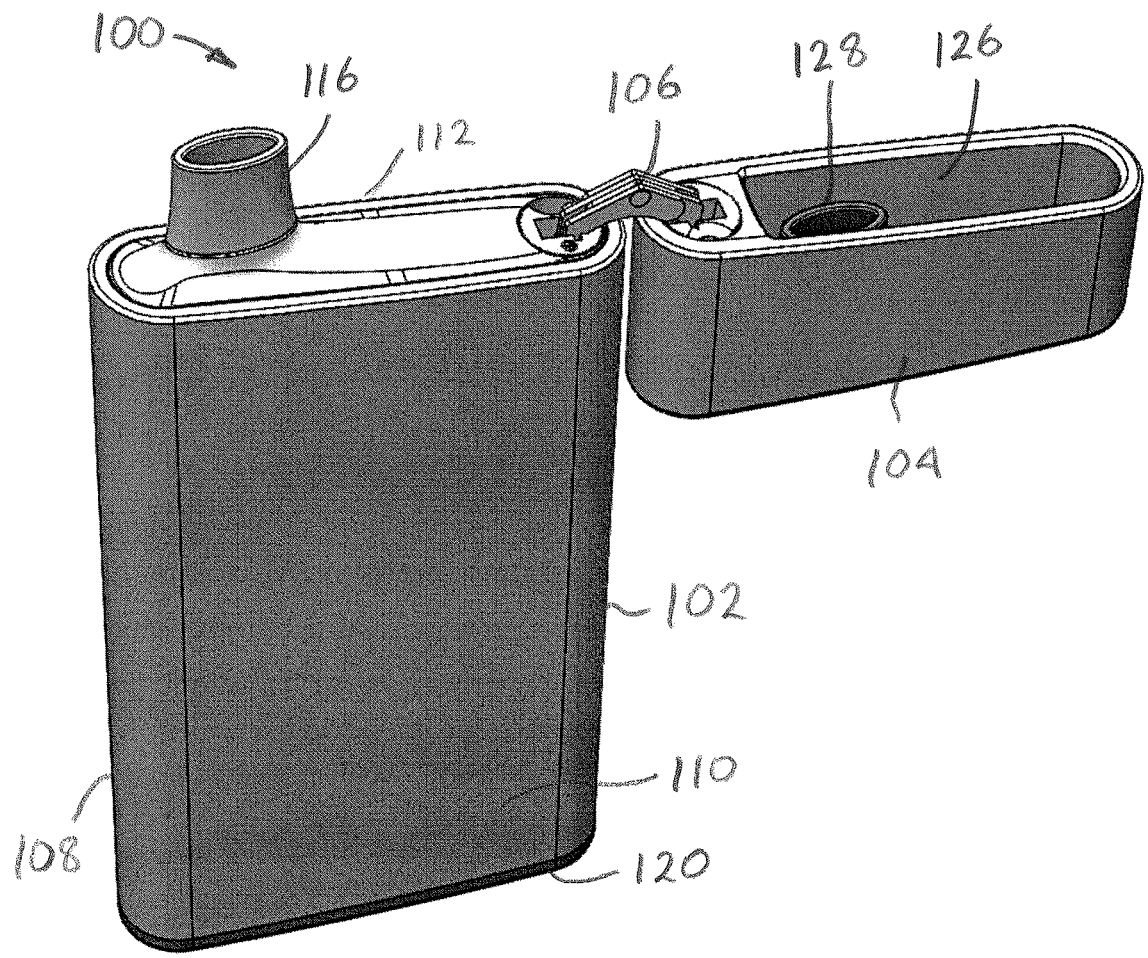
FIG. 13 is a perspective view of the breath sensing device of FIG. 1, showing the device with its pivoting lid in an open position.

Referring to FIGS. 11-13, device 100 may be provided with a spare mouthpiece 128 that can be snapped into place and stored inside lid 104 as shown when not being used. Spare mouthpiece 128 may be identical to mouthpiece 116 and interchangeable therewith so that two users can share a single device 100, or so that a single user can use a clean mouthpiece in between disinfection cycles. Alternatively, mouthpiece 128 may have different size and/or flow characteristics than mouthpiece 116, with the different mouthpieces being used for different types of measurements, testing conditions or users. In the mounting configuration within lid 104 as shown, mouthpiece 128 may be disinfected at the same time as mouthpiece 116 during the same disinfection cycle. UVGI unit 122 or a separate UVGI unit may be configured to disinfect a breath sampling chamber and/or breath flow path 140, which are further described below. In some embodiments, a single UVGI unit 122 is configured to simultaneously disinfect breath sampling chamber and/or breath flow path 140 at the same time as the mouthpieces 116 and 128 described above.

Figure 14:
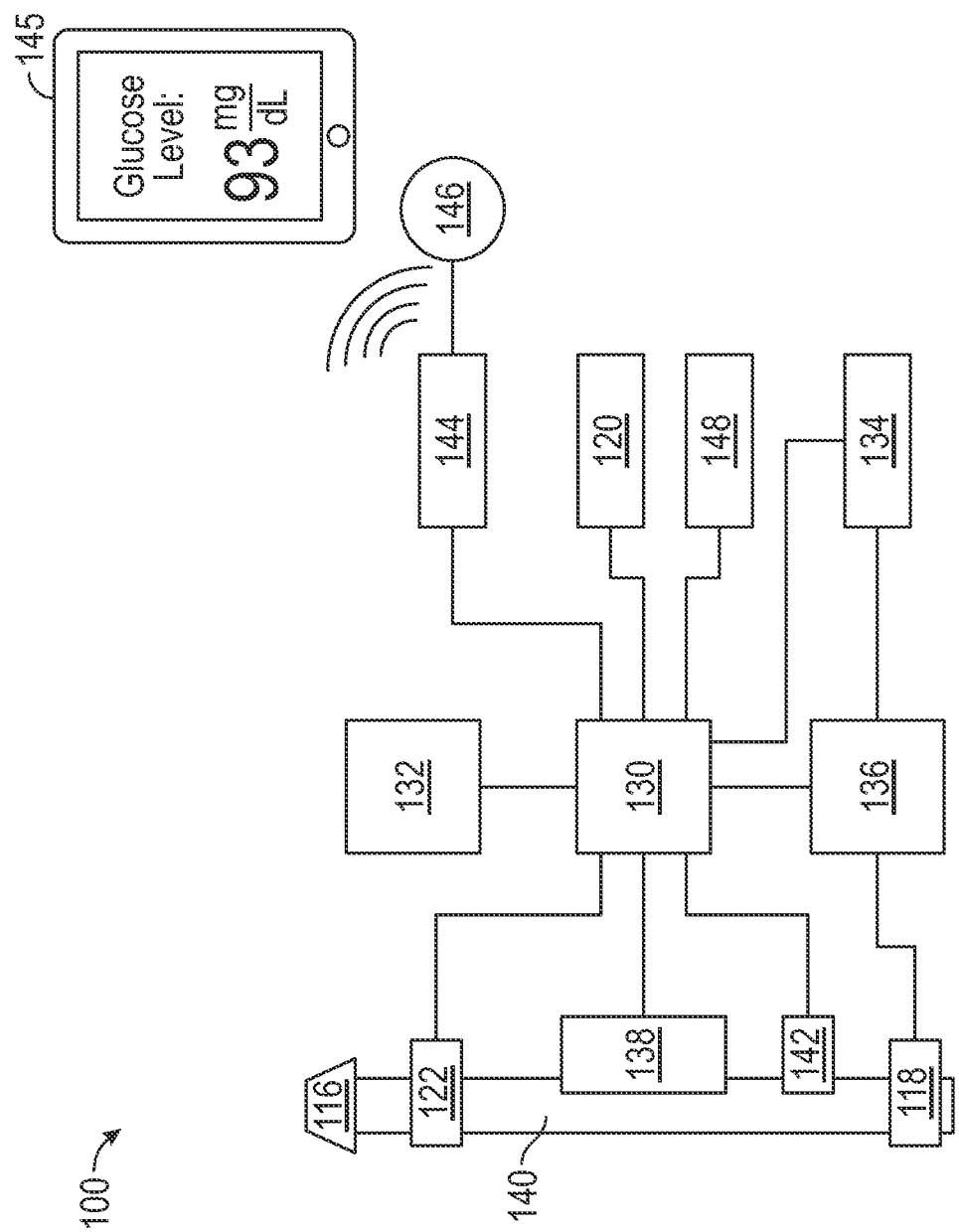
FIG. 14 is a block diagram schematically showing exemplary components of the breath sensing device of FIG. 1.

Referring to FIG. 14, the various internal components of exemplary device 100 are schematically shown. A microprocessor 130 is provided to run the various operations of device 100 and utilizes memory unit 132 for storage. Microprocessor 130 is powered by battery 134, which in turn is charged through charging circuitry 136 and combination exhaust vent and charging port 118. In alternative embodiments, an inductive coupling unit (not shown) may be used instead of or in combination with charging port 118. Previously described LED band 120 is controlled by microprocessor 130, as is ultraviolet germicidal irradiation (UVGI) unit 122. One or more breath sensors 138 are placed in the breath flow path 140 between mouthpiece 116 and exhaust port 118 and communicate with microprocessor 130. Breath flow path 140 may have a serpentine shape, be provided with a breath accumulation, buffer or sampling chamber, a humidity control or sensing device, temperature control or sensing device, and/or other features (not shown) to allow breath sensor 138 to accurately detect biomarkers in the exhaled breath traveling through flow path 140. Device 100 may be provided with an on/off switch or other input devices (not shown), and/or may be activated from an external wireless device. In this exemplary embodiment, microprocessor 130 remains in an energy saving sleep mode until it senses a pressure change in breath flow path 140 with pressure and/or flow sensor 142. A Bluetooth circuit 144 and/or other wireless communication device may also provided to allow device 100 to send information to and/or receive information/instructions from another device such as a smart phone or tablet 145 running a proprietary app associated with device 100. The proprietary app may be configured to display results of measurements performed by device 100 and may allow a user to adjust settings of device 100. A Bluetooth icon or LED indicator 146 may be provided somewhere on the device housing to indicate the status of Bluetooth circuit 144, as further described below. A display (not shown) may be provided on the main housing or device lid for displaying the results of the measurements performed by device 100, or other information. Such a device mounted display may include touchscreen functionality, and/or one or more buttons (not shown) may be provided on device 100 to control its operation. A haptic device 148 may be connected to microprocessor 130 for providing tactile feedback to the user, as further described below.

When exhaled breath is being measured, there are often certain portions of the breath sample that are of more interest than others. For example, the end portion of a tidal breath typically contains fewer contaminates and more of the analytes, VOCs, biomarkers, etc. of interest, or contains these items in a more consistent, repeatable manner. Accordingly, the user of a breath sensor such as device 100 often needs to be instructed how to perform a desired breath maneuver in order to obtain accurate results. The user may need to be instructed during the breath maneuver to exhale faster, slower, longer, etc. such that real-time feedback to the user from the device is useful. Various cues may be used in this regard, such as audible, visual and/or haptic feedback. In the present exemplary device 100, audible feedback is not used, allowing the user to be more discrete when using device 100 in public settings. As described in the first detailed example below, LED band 120 is used to communicate instructions to the user. In the second example below, haptics (vibrations in main housing 102) are used in conjunction with the LED band 120. In some embodiments, LED band 120 may be turned off (such as with a smart phone app) so that only the haptic feedback is used. This permits more discrete use of device 100, such as when the user is in a dimly lit restaurant or theater. In other embodiments, similar visual and haptic feedback schemes may be utilized without departing from the spirit and scope of the present disclosure.

Example 1

Status modes (assuming device 100 is turned on before and turned off after each use):
Off: no active indicators.
Start-up/Warm-up (wait): Pulsing White Illumination on base LED band 120.
Bluetooth:
  Pairing: Pulsing Blue Illumination on Bluetooth icon 146.
  Paired: Solid Blue Illumination on Bluetooth icon 146.
  Pairing Attempted, Not Paired: Solid Red Illumination on Bluetooth icon 146.
Start (Exhalation): Pulsing Blue Illumination on base LED band 120.
Exhalation Strength:
  Low: Solid Blue Illumination (Dim/Faint) on base LED band 120.
  Good: Solid Blue Illumination (Bright) on base LED band 120.
  High: Pulsing Orange/Red Illumination on base LED band 120. (There can be gradual transitions between the Low, Good and High Exhalation Strength indications.)
Stop (Exhalation): Solid White Illumination on base LED band 120.
Processing (wait): Orbiting/Pulsing White Illumination on base LED band 120.
Cleaning (UV Sanitization): Pulsing Violet Illumination on base LED band 120.
Shut Down: 3 Quick Flashes of White Illumination on base LED band 120.

Example 2

The status modes of Example 1 are used, with the following modes used instead of or in conjunction with the same modes in Example 1:
Start (Exhalation): Slow, Repeating Haptic Pulse in main housing 102.
Exhalation Strength:
  Low: Continuous Low Frequency Haptic Feedback in main housing 102.
  Good: Continuous Mid Frequency Haptic Feedback in main housing 102.
  High: Continuous High Frequency Haptic Feedback in main housing 102. (There can be gradual transitions between the Low, Good and High Exhalation Strength indications.)
Stop (Exhalation): 3 Quick Haptic Pulses in main housing 102.

The systems and methods described herein can advantageously allow users to discretely measure their exhaled breath in an easy, cost-effective and non-invasive manner.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the disclosure. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the FIGS. is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" or "disclosure" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A handheld breath sensing system comprising:
    a main housing;
    a first mouthpiece located on the main housing and configured to allow a user to exhale into the first mouthpiece;
    a lid pivotably mounted to the main housing and movable between an open position in which the first mouthpiece is exposed, allowing the user to immediately exhale into upon opening of the lid, and a closed position in which the first mouthpiece is covered;
    a sampling chamber located within the main housing and in fluid communication with the first mouthpiece;
    a sensor in fluid communication with the sampling chamber and configured to measure at least one property of a user's breath in the sampling chamber; and
    a microprocessor electronically coupled to the sensor and configured to process electronic signals from the sensor such that at least one volatile organic compound in the user's breath can be quantified and a resulting biomarker measurement provided to the user,
    wherein the system further comprises a second mouthpiece configured to be interchangeable with the first mouthpiece and wherein an inside portion of the lid is configured to alternately hold the first mouthpiece or the second mouthpiece when the first mouthpiece or the second mouthpiece is not in fluid communication with the sampling chamber allowing the user to exhale through it into the sampling chamber, and
    wherein the main housing and the lid in its closed position provide a closed volume of less than 8.0 cubic inches in which the first mouthpiece, the second mouthpiece, the sampling chamber, the sensor and the microprocessor are housed.

2. The system of claim 1, wherein the biomarker measurement is a glucose level.

3. The system of claim 1, wherein the biomarker measurement is a ketone level.

4. The system of claim 1, wherein the system further comprises a wireless communication device electronically coupled to the microprocessor thereby allowing the microprocessor to wirelessly communicate with another mobile device.

5. The system of claim 4, wherein the other mobile device is a smart phone running a proprietary application associated with the handheld breath sensing system, the application being configured to display the biomarker measurement to the user.

6. The system of claim 1, wherein the system further comprises a display located on the main housing or lid, the display being electronically coupled to the microprocessor and configured to display the biomarker measurement to the user.

7. The system of claim 1, wherein the system further comprises an ultraviolet germicidal irradiation unit configured to emit a short-wavelength ultraviolet light to kill or inactivate microorganisms located on one or more surfaces of the first mouthpiece.

8. The system of claim 7, further comprising a light guide located between the ultraviolet germicidal irradiation unit and the first mouthpiece, the light guide configured to guide light from the irradiation unit to the first mouthpiece.

9. The system of claim 8, wherein the ultraviolet germicidal irradiation unit is configured to emit a short-wavelength ultraviolet light to kill or inactivate microorganisms located on one or more surfaces of a second mouthpiece located in the lid simultaneously with the first mouthpiece.

10. The system of claim 1, wherein the system further comprises an ultraviolet germicidal irradiation unit configured to emit a short-wavelength ultraviolet light to kill or inactivate microorganisms located on one or more surfaces of the sampling chamber.

11. The system of claim 10, wherein the ultraviolet germicidal irradiation unit is configured to emit a short-wavelength ultraviolet light to kill or inactivate microorganisms located on one or more surfaces of the first mouthpiece simultaneously with the sampling chamber.

12. The system of claim 11, wherein the ultraviolet germicidal irradiation unit is configured to emit a short-wavelength ultraviolet light to kill or inactivate microorganisms located on one or more surfaces of a second mouthpiece located in the lid simultaneously with the sampling chamber and the first mouthpiece.

13. The system of claim 12, wherein the sampling chamber, the first mouthpiece and the second mouthpiece are arranged such that the sampling chamber, the first mouthpiece and the second mouthpiece may all be disinfected simultaneously in a single disinfection cycle, and wherein the first mouthpiece receives at least some of the short-wavelength ultraviolet light directly from the ultraviolet germicidal irradiation unit and the second mouthpiece receives the short-wavelength ultraviolet light indirectly from the ultraviolet germicidal irradiation unit after the light reflects off of an inside surface of the lid.

14. The system of claim 1, wherein the system further comprises a multi-pivot hinge configured to pivotably connect the lid to the main housing such that there are no hinge parts protruding from the lid and the main housing when the lid is in the closed position.

15. The system of claim 14, wherein there are no hinge parts visible from an exterior perspective of the lid and the main housing when the lid is in the closed position.

16. A method of sensing a biomarker exhaled from a user, the method comprising:
providing a handheld breath sensing system as recited in claim 1;
pivoting the lid into the open position;
exhaling into the first mouthpiece;
using the sensor to measure at least one property of the user's breath in the sampling chamber;
using the microprocessor to process the electronic signals from the sensor such that the at least one volatile organic compound in the user's breath is quantified; and
providing the resulting biomarker measurement to the user.

17. The method of claim 16, further comprising establishing wireless communications between the microprocessor and a smart phone running a proprietary application associated with the handheld breath sensing system, and using the application to display the biomarker measurement to the user.

18. The method of claim 16, further comprising using a display mounted on the main housing or the lid to display the biomarker measurement to the user.

19. The method of claim 16, further comprising activating an ultraviolet germicidal irradiation unit to emit a short-wavelength ultraviolet light to kill or inactivate microorganisms located on one or more surfaces of the first mouthpiece.

20. The method of claim 19, further comprising activating the ultraviolet germicidal irradiation unit to emit a short-wavelength ultraviolet light to kill or inactivate microorganisms located on one or more surfaces of a second mouthpiece located in the lid simultaneously with one or more surfaces on the sampling chamber and the first mouthpiece.

* * * * *